United States Patent [19]
Hoffman

[11] Patent Number: 5,769,630
[45] Date of Patent: Jun. 23, 1998

[54] SUBPERIOSTEAL BONE ANCHOR

[75] Inventor: David R. Hoffman, deceased, late of Mandeville, La., by Joan M. Hoffman, executrix

[73] Assignees: Louisiana State University,, Baton Rouge; Darman, Inc, Metaire, both of La.

[21] Appl. No.: 679,338

[22] Filed: Jul. 11, 1996

Related U.S. Application Data

[63] Continuation-in-part of Ser. No. 143,711, Nov. 1, 1993, Pat. No. 5,538,427, which is a continuation-in-part of Ser. No. 792,855, Nov. 18, 1991, abandoned, which is a continuation-in-part of Ser. No. 659,680, Feb. 25, 1991, Pat. No. 5,066,224.

[51] Int. Cl.$^6$ ...................................................... A61C 3/00
[52] U.S. Cl. .................................. 433/7; 433/18; 433/24; 433/173; 623/16
[58] Field of Search ................................... 433/7, 18, 23, 433/24, 173, 174, 175, 176, 172, 201.1; 623/16, 18, 20

Primary Examiner—Nicholas D. Lucchesi
Attorney, Agent, or Firm—John T. Roberts

[57] ABSTRACT

A subperiosteal bone anchor used in two distinct applications; as an orthodontic anchor system, and as an orthopedic anchor system. As an orthodontic anchor system, it is used for treatment of growth disharmony and malalignment of the teeth in which the subperiosteal bone anchor is surgically placed in the subperiosteal tunnel on skeletal bone allowing osseointegration between the subperiosteal bone anchor bone interface and the bone. After osseointegration a palatal bar or palatal wire is attached to the orthodontic anchor system and attached to bands around one or more teeth, holding them immobile. As an orthopedic anchor system the subperiosteal bone anchor is used to stabilize devices which need to be anchored to a bone, or to transmit attractive or distractive forces to a bone for reconstruction or transformation.

18 Claims, 9 Drawing Sheets

SUBPERIOSTEAL BONE ANCHOR

CROSS-REFERENCE TO RELATED APPLICATION

This invention is disclosed in part in our application entitled SUBPERIOSTEAL BONE ANCHOR, application Ser. No. 08/143,711, filed on Nov. 1, 1993 now U.S. Pat. No. 5,538,427. This invention is also disclosed in part in our application entitled BONE ANCHOR, application Ser. No. 07/792,855, filed on Nov. 18, 1991, now abandoned. The invention is also disclosed in part in our patent application entitled ORTHODONTIC ANCHOR, application Ser. No. 07/659,680, filed Feb. 25, 1991, now U.S. Pat. No. 5,066,224, issued Nov. 19, 1991. The priority of each of these is claimed for the common subject matter.

BACKGROUND OF THE INVENTION

Skeletal deformities become evident during the growth of an individual or may be acquired from events such as trauma, tumor resection, or systemic disease.

Correction of bone deformities may require surgical treatment to reposition the deformed bones into a "normal" relationship or by orthopedically guided bone movements. Currently, pins or other transosseous devices are used in conjunction with some surgical procedures to anchor or move the bones and to maintain bone position during treatment and healing. These transosseous devices penetrating into the medullary bone have limitations in some regions of the human skeleton. In the jaw bone, there are tooth roots and developing tooth buds in the juvenile which may prevent pins from being used. The correction of facial deformities presents clinical challenges which have led to this invention. In other areas, such as the skull, the bone is too thin to stabilize a transosseous device. If or when pressure is applied, the pins will dislodge and preclude correction of the cranial deformity.

Often, the earliest signs of maxillary (upper jaw) or mandibular (lower jaw) growth disharmony is dental malalignment. Once recognized, it is possible to guide the growth of the segments of the cranio-facial skeleton to minimize the need for surgical correction of the deformity. Maxillary hypoplasia (deficiency) exists in all three dimensions. Transverse deficiency of the maxilla is commonly treated by orthodontists with orthopedic palatal expansion. Morphologically, this is possible due to the existence of a patent mid-palatal suture. Deficiency in the maxilla in the vertical or anterior-posterior (A-P) direction has not been satisfactorily performed by orthopedically guided movements because a lack of an existent transverse suture line. Orthodontists employ orthopedic traction primarily in the A-P dimension to control or direct the development of the mandibular jaw bone to a favorable position. Mandibular deficiency can be corrected by functional appliances which position the mandible forward and presumably allow for a posterior condylar appositional growth which stabilizes the mandible in this forward position.

Cleft palate patients often have transverse, anterior-posterior, and vertical dysplasia of the maxilla. Treatment of these patients often involves orthodontic alignment of the alveolar (tooth bearing) segments prior to bone grafting the alveolar defects. However, the defects can be large and difficult to manage when the patient is young. The deciduous dentition can also be difficult to manage since there is inadequate orthodontic anchorage. This can prevent definitive alignment of the arches until the patient is in the early teens. All orthodontic and orthopedic forces adhere to Newton's "Law of Reciprocal Forces." If a force is applied to retract or pull back an object such as a tooth, there exists an "equal and opposite" force to move another tooth or object forward. The resistive value of the teeth is known as anchorage. Orthodontists may offset these reciprocal tendencies by using an extraoral force known as a headgear to augment the resistive value of the teeth.

However, patient compliance is often inadequate. Many patients do not want to wear the headgear, compromising orthodontic therapy and often the final result. Orthodontic forces are usually continuous, acting 24 hours a day. Realistically, most patients will not wear headgear more than 10–12 hours/day. Therefore, the posterior anchorage is typically fortified 40–50% of the time. All too often, inconsistent usage or overt noncompliance will reduce this effect even more. The trans-palatal arch wire or bar by itself will cause reciprocal forces between the teeth to which the wire is attached. It will not implant special properties to these teeth beyond the simple additive values of the same two teeth. Both orthodontists and their patients will welcome a device which is simple to install, obviates the necessity to wear extraoral devices, helps to decrease the total time, and permits a more predictable result.

Previous work in this field indicates that endosseous implants can be used to anchor orthodontic forces for tooth movement. These studies indicate that osseointegrated implants have been used to anchor realignment of the teeth without reciprocal movement by the implants. All of these implants were placed deeply into the bone.

Endosseous implants are not suitable in juvenile or adolescents for two reasons. First and foremost, endosseous implants are inserted into a hole which is drilled into the alveolar (tooth bearing) portion of the jawbone. Insertion of an endosseous implant into these areas will harm unerupted teeth which are forming in these areas. Since the juvenile and adolescent patients are still growing, an endosseous implant will be engulfed with continuing vertical development of the alveolar bone and would progressively sink to a lower level to the point that it becomes inaccessible, not useful, and inherently difficult to remove.

In juveniles or adolescents with skull deformity the neurosurgeon or plastic surgeon is often faced with a very difficult, high-risk surgery to incise the skull and abruptly reposition the cranial bones. This almost always involves communication with the brain cavity and carries with it the grave risks associated with such procedures. Transosseous pins to anchor expansion devices in the cranium are contraindicated because they would penetrate into the dura or sinusoids, or because of the thinness of the cranium, the pins would dislodge and fail to anchor the required bone movements. The use of transosseous pins in small bones such as the hands is precluded because of the size limitation of the pins being larger than the medullary cavity of the intended bones.

In orthopedic surgery it is sometimes necessary to attach devices to a bone. In the case of trauma, this may be necessary to stabilize the fragments while healing occurs. In other cases, it is desirable to apply fores to a bone which is deficient in size or misshapen. There is a technique called distraction osteogenesis (DO) which allows a bone to be stretched with an expansion device after the cortical surface has been incised.

To stabilize these devices, threaded pins are inserted deeply into the bone. These pins are known as transosseous pins. They work well in long bones but there exists a need to attach devices to thin bones such as the skull or mandible.

This subperiosteal bone anchor has been successfully tested in this regard and will allow surgeons to attach devices to small or thin bones using surface adherent technology.

The objectives of this invention can be stated as follows.

1. It must not deeply enter the bone, but should attach to the cortical surface.

2. It should be thin to lay under the soft tissue against the bone without creating significant inflammation or bulk.

3. It should have versatility of attachments in order to assume a role for an orthodontic anchor, an orthopedic anchor, or attach other devices to a bone such as a pacemaker, hearing aid, prosthesis, insulin pump, or other medical or dental devices.

4. It must have sufficient shear strength, to resist forces placed upon it from orthodontic or orthopedic devices or to stabilize devices that maybe attached to it.

THE PRIOR ART

The use of implants to replace missing teeth is mentioned in ancient documents. In modern dentistry a resurgence of interest in the use of endosseous implants occurred in the 1950's.

The only two types of anchoring systems for orthodontic device in the prior art are the generations old banding of teeth and using them as anchors, and the more recent use of cylindrical endosseous implant as anchors. These endosseous implants are either uncoated or coated implants.

The Brånmark System®, introduced in the early 1980's, has shown that an endosseous implant of commercially pure titanium may be used as an abutments for orthodontic devices. When the implant is allowed to rest unloaded for sufficient time, osseointegration occurs, Brånmark, Zarb, Albrektsson, *Tissue-Integrated Prostheses*, Quintessence Books 1985.

Clinically, hydroxylapatite coated cylindrical endosseous implants have been in place since 1984; Kent J. N., Block M. S., et al.: *Biointegrated hydroxylapatite coated dental implants five year clinical observations*. J Amer Dent Assoc., accepted 1990. Almost all studies have shown that coated endosseous implants have more bone contact a substantial period after implantation than uncoated implants.

U.S. Pat. No. 4,379,694, Apr. 12, 1978, Riess discloses two forms of coated endosseous implants. One form is a flat metal plate with a saddle shape which is inserted into a depression formed by cutting into the bone ("milling prep of the bone"). This is therefore an endosseous implant, since it is inserted below the original outer surface of the jawbone. Around the plate is a coating of a minor part of poly methyl methacrylate (PMMA) and a major part of resorbable sintered tricalcium phosphate.

Both versions of the Riess implant have a series of apertures in the surface into which are inserted tablets of tricalcium phosphate. It is well known that tricalcium phosphate eventually is resorbed in bone, as acknowledged by Riess, and Riess states that bone grows into these apertures. This growth of bone into the apertures would form a stable mechanical lock, making irrelevant any other type of bonding of the implant to the bone.

One article, citing its findings and an earlier study, reports that detaching tests showed that the average failure load of β-TCP blocks to be not significantly different than hydroxylapatite, and that β-TCP bonded directly to bone without intervening fibrous tissue, Kotani S, Fujita T, Nakamura T, Yamamuro T, *Bone Bonding mechanism of β-tricalcium phosphate*, J. Bio. Mat. Res. 25:1303–1315, 1991.

A subperiosteal implant has heretofore not been used to anchor a orthodontic device in humans. The subperiosteal implants used in humans have been limited to endentulous patients, where existing teeth do not interfere with the placement of the implant on the jawbone, where those implants have been merely onlayed onto the bone. The subperiosteal implants in humans have have been used to anchor one or more artificial teeth, where the principal force is compressive, and not in shear as is the case for an anchor, so the implant does not need to resist those forces.

In situations where due to a loss of bone, an endosseous implant is contraindicated, a subperiosteal implant has been used. A metal plate is cast to fit over the bone but beneath the gum or periosteum. Such an implant is shown in U.S. Pat. No. 4,693,686, Sep. 15, 1987, Sendax. A smaller prefabricated subperiosteal implant made of a pliable metal plate is disclosed in U.S. Pat. No. 4,702,697, Oct. 27, 1987, Linkow.

In a few reported cases in the prior art classic subperiosteal implants, used to anchor artificial teeth, and coated with hydroxylapatite were implanted in human jawbones and a bond with the bone was fouund when the implant was removed.

SUMMARY OF THE INVENTION

As a orthodontic anchor system for treatment of growth disharmony, bone deformity, bone atrophy, and malalignment of the teeth, a subperiosteal bone anchor is surgically placed in a subperiosteal tunnel on skeletal bone, allowing osseointegration between the subperiosteal bone anchor-bone interface and the bone. Once the subperiosteal bone anchor has integrated with the bone, various devices or abutments are attached to the subperiosteal bone anchor. The attachment may consist of a palatal bar, a wire, expansion devices, or other devices which may be attached to teeth, attached to either extraoral or intraoral traction devices to move or orthopedically reposition the bone segments, or other orthopedic load systems to reposition the bone.

As an orthopedic anchor the subperiosteal bone anchor is surgically placed in a subperiosteal tunnel on a skeletal bone allowing osseointegration to occur between the subperiosteal bone anchor and bone surface. After osseointegration has occurred, devices may be attached to the subperiosteal bone anchor with the purpose of guiding movement of the bones that the subperiosteal bone anchors are osseointegrated with to bring the bones closer or further apart for the correction of bone deformities.

The subperiosteal bone anchor may also be osseointegrated with the bone and used to anchor various other medical or prosthetic devices. The categories of this type include, but is not limited to, cardiac pacemakers, insulin pumps, cardiac defibrillators, hearing aids, prosthetic moulages, etc.

The invention accordingly comprises the several steps and the relation of one or more of such steps with respect to each of the others, and the apparatus embodying features of construction, combinations of elements and arrangements of parts which are adapted to effect such steps, all as exemplified in the following detailed disclosure, and the scope of the invention will be indicated in the claims.

BRIEF DESCRIPTION OF THE DRAWINGS

The invention will be better understood and the objects other than those set forth above will become apparent when consideration is given to the following detailed description thereof. Such description makes reference to the annexed drawings wherein.

DESCRIPTION OF THE PREFERRED EMBODIMENTS

A. Orthodontic Applications

The orthodontic anchor system (20) has two parts; the subperiosteal bone anchor (21) and the abutment (22). These are connected to a palatal bar (24) or palatal wire (28), which is attached to crowns or bands (25) around the teeth to be held immobile. The abutment, the palatal bar and palatal wire as illustrated are commonly used in orthodontic treatment.

Figure 15:
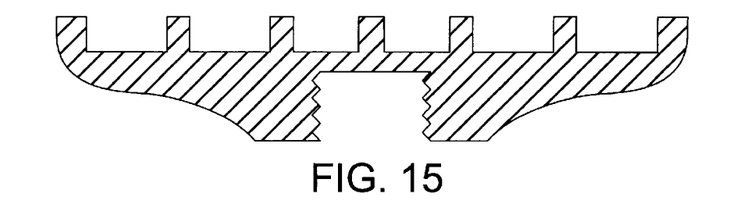
FIG. 15 shows a cross sectional view, an alternative embodiment of the underneath surface of the invention with an annular grooved surface.

As shown in FIGS. 1 through 4, the subperiosteal bone anchor (21) has a circular surface (30) which is the bone interface. The circular flat shape is illustrative only. The subperiosteal bone anchor may be oval, square, rectangular, triangular, or any other shape to resist the forces applied to it. It may be preformed to have a concave or convex shape of lesser or greater radii to fit the contour of the bone surface to which it will be applied. This bone interface (30) is illustrated with a regularly pyramidal-shaped texture which both increases the surface area and is better able to resist the sheer forces imposed by the orthodontic or orthopedic forces. It is anticipated that other designs may be more resistant to shear forces. An annular groove design is illustrated in FIG. 15 as an alternative embodiment. This embodiment is disclosed conceptually. The number and size of the grooves may be varied from the shape shown. The subperiosteal bone anchor (21) has a surface with a beveled outer portion (31) and a central circular portion (36). The outer portion (31) joins the outer periphery of the anchor bone interface (30). The center of the lower surface (36) has at least one threaded aperture (32). There may be more than one threaded aperture depending on the need to resist rotational forces. When the subperiosteal bone anchor is initially installed, the threaded aperture (32) has a conventional healing screw, not shown, installed to prevent connective tissue from invading the aperture.

The first bone anchor tested by the inventors was 8 mm. in diameter (50 square millimeters). It withstood 160 lbs. of shear pressure before failing. Most orthodontic and orthopedic force loads are in the 6 oz. to 20 lb. range, and generally in a shear mode. Therefore it is anticipated that even smaller sizes of 4–6 mm in diameter (10–30 square millimeters) will be adequate. The smaller size offers a great advantage in being easier to insert and less susceptible to bone surface topographical variations. It is also anticipated that larger sizes of 150 square millimeters or greater may be required to resist torsional forces.

The structure of the subperiosteal bone anchor (21) is of titanium alloy. It is anticipated that other suitable materials may be used instead. These will include metals, plastics, and composites. The surface, except for the subperiosteal bone anchor bone interface (30), is smooth. The periphery is thin and bevelled to prevent damage to soft tissue.

The test sample of subperiosteal bone anchor had a 50 micron coating of calcium hydroxylapatite. The coating may vary in thickness and the surface may have a osseoactive coating other than calcium hydroxylapatite. The calcium hydroxylapatite coating was plasma sprayed on the metal using conventional practices. This spray consists of a super heated solution of hydroxylapatite applied to the roughened titanium alloy.

Figure 1:
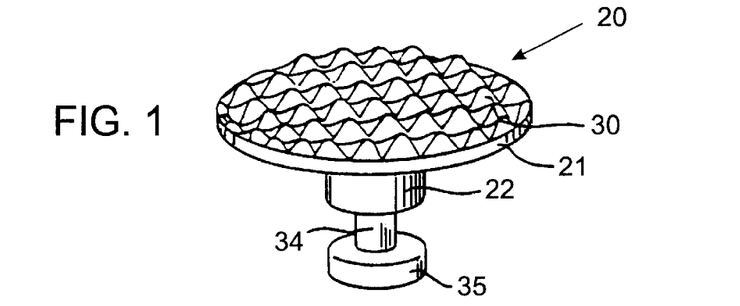
FIG. 1 is a perspective view of the invention showing one possible abutment attached.
Figures 2, 3, 4:
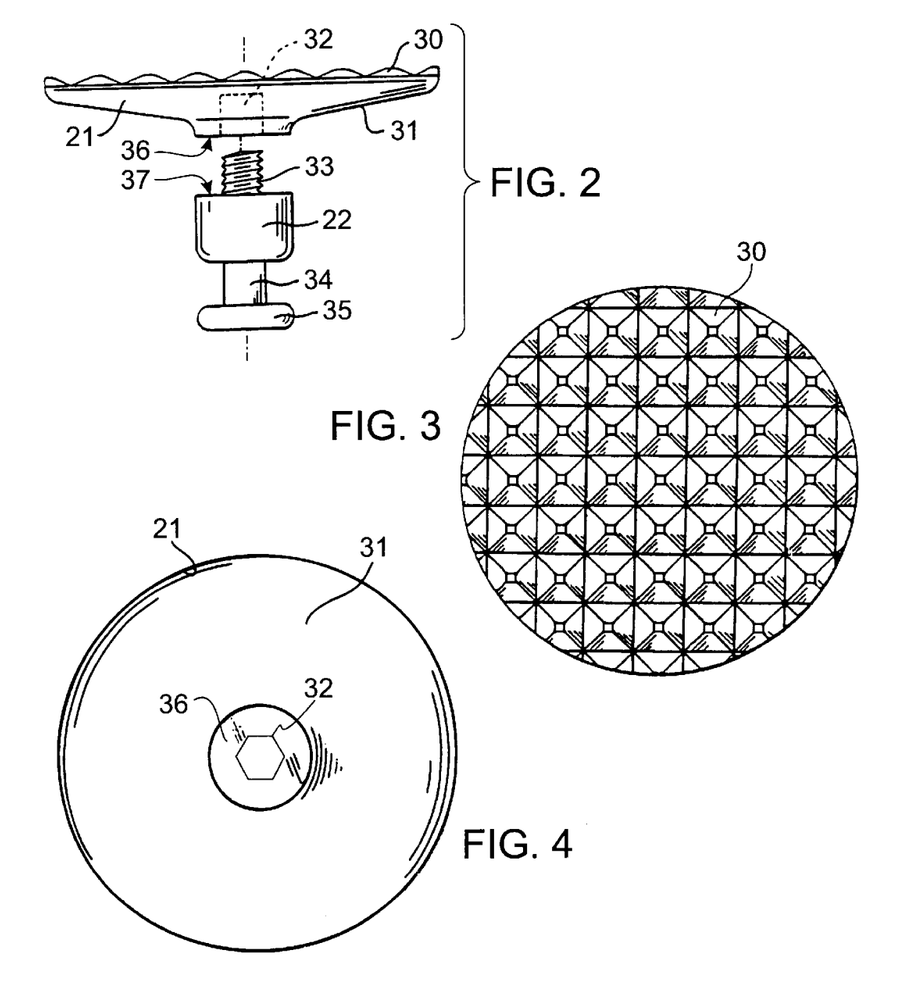
FIG. 2 is an exploded side elevation view of the invention and abutment of FIG. 1.
FIG. 3 is a underneath view of the invention of FIG. 1.
FIG. 4 is a surface view of FIG. 1 demonstrating the threaded aperture.
Figure 5:
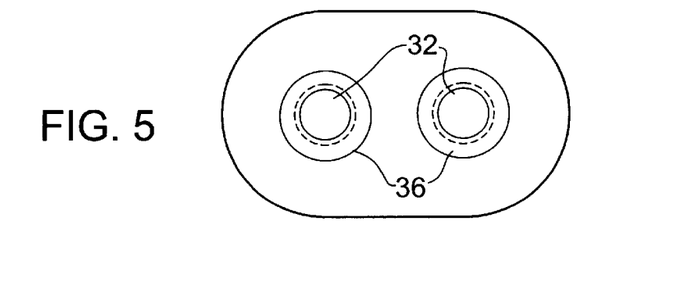
FIG. 5 is a surface view of an alternative embodiment of the invention demonstrating two threaded apertures.

FIG. 5 is similar to FIG. 4 but is oval in shape and has two threaded apertures (32). This embodiment permits two attachments to the same device. This may be useful to prevent rotational or torquing reactions.

Figure 6:
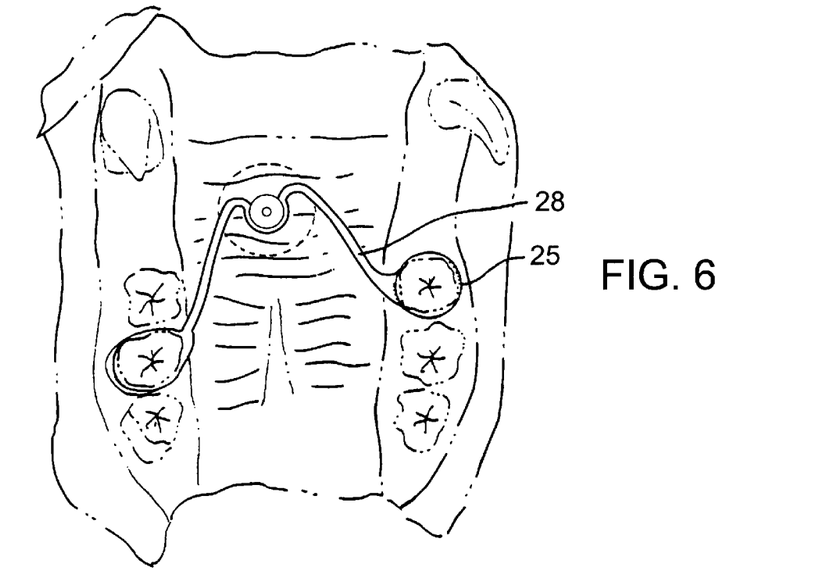
FIG. 6 is an intraoral view with the invention and a type of abutment with a palatal wire connected to two banded teeth.

As shown in FIG. 6, the palatal wire (28) is soldered to the two bands (25) of two molars or other teeth and presses against the neck (34) of the abutment (22). This palatal wire (28) may be fabricated from a 0.051 in. stainless steel orthodontic wire.

Figure 7:
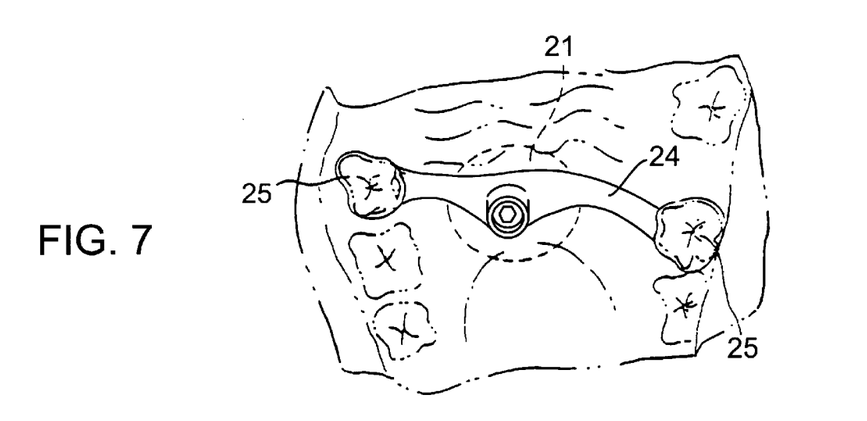
FIG. 7 is an intraoral view of the invention and a type of abutment with a cast palatal bar attached to two banded teeth.

FIG. 7 shows the cast palatal bar (24) which is soldered to the two bands (25) cemented to molar teeth. This palatal bar (24) is screwed to a conventional prosthetic abutment which is screwed into the subperiosteal bone anchor (21). The cast palatal bar is more rigid and may be useful for critical control of the anchorage, higher force levels, or to distallize one or more teeth.

Figure 8:
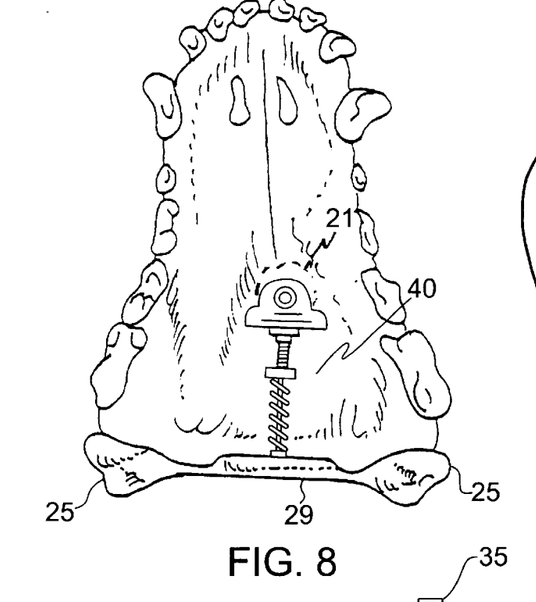
FIG. 8 shows the invention connected to a type of abutment which is soldered to an orthodontic expansion device connected to two molar teeth.

FIG. 8 shows an subperiosteal bone anchor (21) connected to an orthodontic expansion device (40) which is connected to a solid transpalatal bar (29) soldered to bands (25) on two molar teeth. Activation of the expansion device (40) will push the molars to which the bands (25) are cemented distally.

FIGS. 16 to 20; 27 to 29; 33 to 38 and 41 disclose an alternative embodiment of. The principal components of this embodiment are a subperiosteal bone anchor 102, an abutment 120, an abutment screw 140, an cylinder 150, a cylinder screw 170, and, a cover screw 180.

The subperiosteal bone anchor 102 is generally similar to the subperiosteal bone anchor 21 shown in FIGS. 1–4. There is a bone interface surface 103, 7.7 mm², an external cylindrical surface 106, a tapered outer portion 107, an external upper plane surface 108 and an external hex surface 109. Depending from the center of the external hex surface 109 is a threaded aperture 111.

Figure 17:
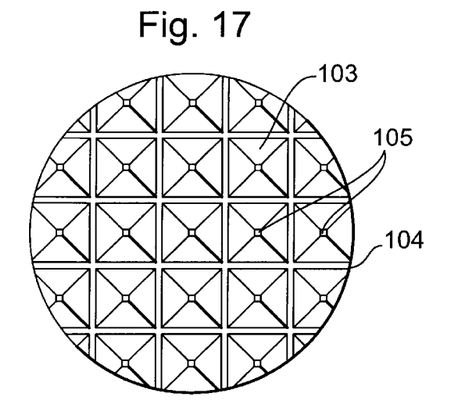
FIG. 17 is a bottom view of the subperiosteal bone anchor 102 of FIG. 16.
Figure 18:
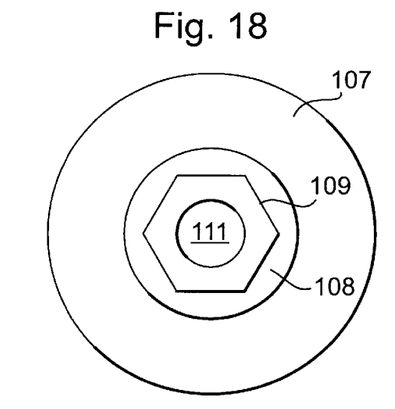
FIG. 18 is a top view of the subperiosteal bone anchor 102 of FIG. 16.
Figure 19:
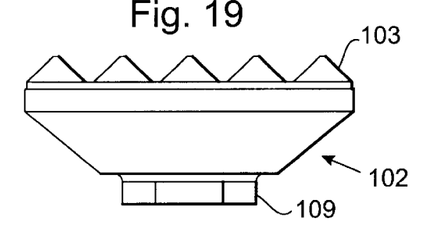
FIG. 19 is a side view, inverted, of the subperiosteal bone anchor 102 of FIG. 16.
Figure 20:
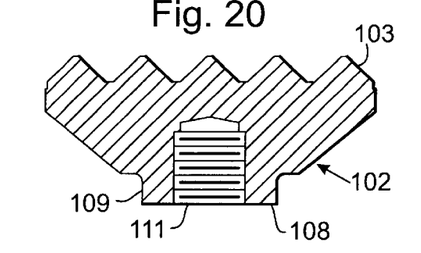
FIG. 20 is a cross sectional view of the subperiosteal bone anchor 102 of FIG. 19.
Figure 21:
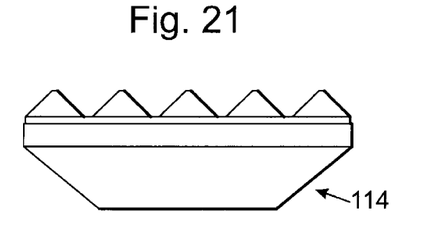
FIG. 21 is a side view of an alternative embodiment of the present invention, a subperiosteal bone anchor 114.
Figure 22:
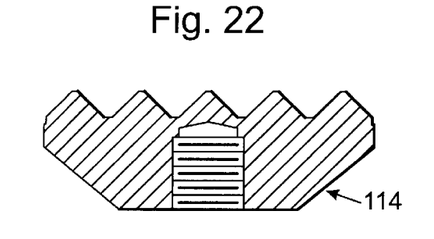
FIG. 22 is a cross sectional view of of the subperiosteal bone anchor 114 of FIG. 21.

The bone interface surface 103 of subperiosteal bone anchor 102 has spaced cross-cut grooves 104 forming uniform pyramids 105, 1.6 mm², each with a slope of 45°. There is a central pyramid, surrounded by nine complete pyramids, and 16 partial pyramids. The bone interface surface 103 is coated with calcium hydroxylapatite.

Figure 33:
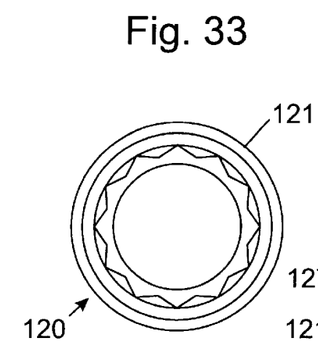
FIG. 33 is a top view of the abutment 120 of FIG. 16.
Figure 34:
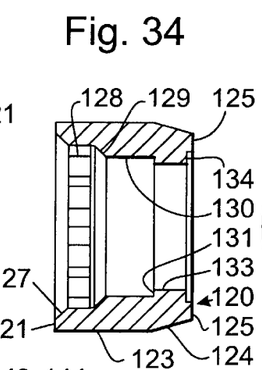
FIG. 34 is a cross sectional view, partially in section, of the abutment 120 of FIG. 33.
Figure 35:
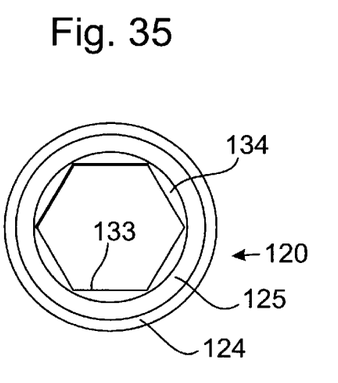
FIG. 35 is a bottom view of of the abutment 120 of FIG. 33.

The abutment 120 is generally cylindrical with a central aperture or bore. The abutment 120 has an external upper plane surface 121, below which is an external cylindrical surface 123, below which is a external tapered surface 124. Below the external tapered surface 124 is the external lower plane surface 125.

Adjoining the inner edge of the external upper plane surface 121, and at the top of the aperture is a internal upper tapered surface 127, leading to a internal dodecadon surface 128, below which is a internal lower tapered surface 129, a internal upper cylindrical surface 130 and a internal upper plane surface 131. Below the internal upper plane surface 131 is a internal hex surface 133, below which is a internal lower plane surface 134, below which is a internal lower cylindrical surface 135 which adjoins the external lower plane surface 125. The internal dodecadon surface 128 and the internal upper plane surface 131 are offset at 15° for a reason explained below.

Figure 16:
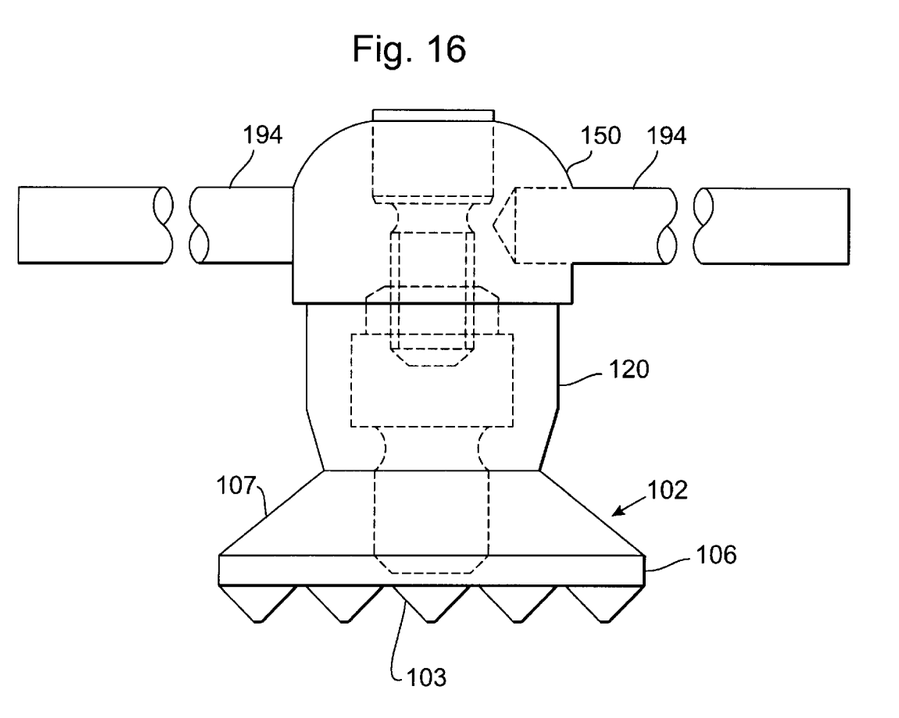
FIG. 16 is a front view of an alternative embodiment of the present invention, showing a subperiosteal bone anchor 102, an abutment 120, a cylinder 150, and a cylinder screw 170 and abutment screw 140, partially in section.

The external lower plane surface 125 rests on the external upper plane surface 108 of the subperiosteal bone anchor 102. The internal hex surface 133 fits over over the external hex surface 109 of the subperiosteal bone anchor 102, preventing either lateral or rotational movement of the abutment 120, with respect to both the subperiosteal bone anchor 102 and the bone of the patient, when locked in position as explained below.

Figure 36:
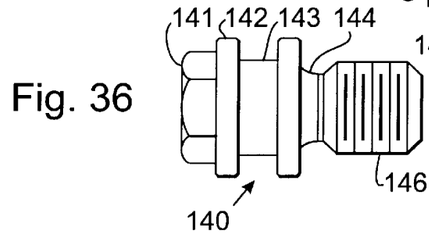
FIG. 36 is a side view, rotated, of the abutment screw 140 of FIG. 16.
Figure 37:
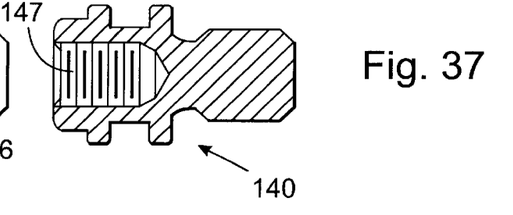
FIG. 37 is a cross sectional view of of the abutment screw 140 of FIG. 36.

The abutment screw 140 has at the top an external hex surface 141, below which is an external cylindrical surface 142, in which is a external cylindrical groove 143. Below the external cylindrical surface 142 is an external neck 144, below which is an external threaded stem 146. Depending from the external hex surface 141 is a internal threaded aperture 147.

A conventional 0-ring (not shown) fits within the external cylindrical groove 143 of the abutment screw 140. The abutment screw 140 fits in sliding engagement within the aperture of the abutment 120, the external cylindrical surface 142 mating with the internal upper cylindrical surface 130 of the abutment 120. The surface below the external cylindrical surface 142 rests on the internal lower plane surface 134 fo the abutment 120. The external threaded stem 146 goes through the aperture of the abutment 120, and is screwed in the threaded aperture 111 of the subperiosteal bone anchor 102, by tightening the external hex external hex surface 141. The top of the external hex surface 141 protudes above the top of the abutment 120 so the orthodontist may fasten the abutment screw 140 onto the subperiosteal bone anchor 102. When the abutment screw 140 is tightened, the 0-ring is compressed, preventing saliva from collecting in the threaded aperture 111 of the subperiosteal bone anchor 102, below the external upper plane surface 108.

Figure 27:
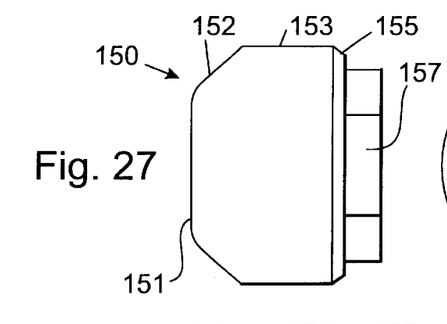
FIG. 27 is a side view, rotated, of the cylinder 150 of FIG. 16.
Figure 28:
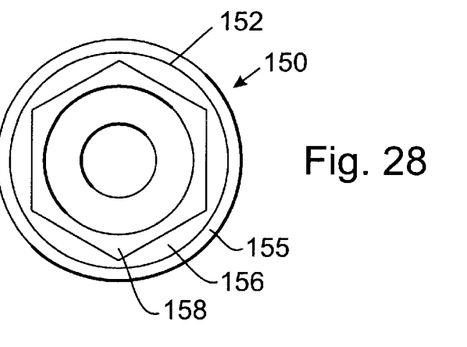
FIG. 28 is a bottom view of the cylinder 150 of FIG. 16.
Figure 29:
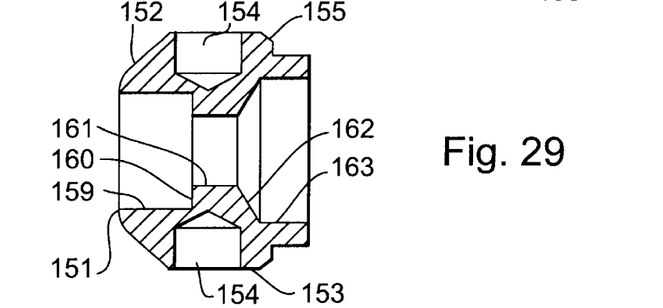
FIG. 29 is a cross sectional view of of the cylinder 150 of FIG. 27.

The cylinder 150 has an external upper plane surface 151, below which is an external upper tapered surface 152 and a external upper cylindrical surface 153. In the sides of the external upper cylindrical surface 153 are horizontal apertures 154, into which fit conventional orthodontic wire 194 or parts of an orthodontic device. Below the external upper cylindrical surface 153 is a external lower tapered surface 155, and a external middle plane surface 156. Below the external middle plane surface 156 is an external hex surface 157, below which is an external lower plane surface 158.

Going through the axis of the cylinder 150 is an aperture, having a internal upper cylindrical surface 159, a internal upper plane surface 160, an internal middle cylindrical surface 161, an internal tapered surface 162, and a internal lower cylindrical surface 163.

The external lower plane surface 158 of the cylinder 150 rests on the external upper plane surface 121 of the abutment 120. The internal lower cylindrical surface 163 fits over the external hex surface 141 of the abutment screw 140. The diameter of the internal lower cylindrical surface 163 is greater than the maximum diameter of the external hex surface 141 so that the rotational position of the external hex surface 141 does not affect the rotational position of the cylinder 150.

The external hex surface 157 of the cylinder 150 interlocks with the internal upper plane surface 131 of the abutment 120. If the abutment 120 remains locked in position, the cylinder 150, and consiquently the orthodontic device, can be locked in 12 positions, at 30° increments. Since the internal dodecadon surface 128 and the internal hex surface 133 of the internal upper cylindrical surface 130 are offset at 15°, the internal upper cylindrical surface 130 and cylinder 150 can be simultaneously rotated and interlocked at 24 different rotational positions, at 15° increments.

Figure 41:
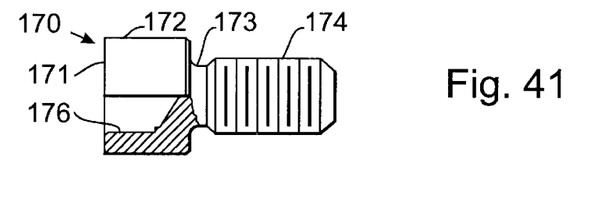
FIG. 41 is a side view, rotated, partially in section, of the cylinder screw 170 of FIG. 16.

The cylinder screw 170 has an external upper plane surface 171, an external upper cylindrical surface 172, an external neck 173 and an external threaded stem 174. Depending from the external upper plane surface 171 is an internal hex surface 176. The cylinder screw 170 fits into, and through, the aperture of the cylinder 150.

The bottom of the external upper cylindrical surface 172 rests on the internal upper plane surface 160 of the cylinder 150. The external threaded stem 174 is screwed into and mates with the internal threaded aperture 147 of the abutment screw 140. The orthodontist tightens the cylinder screw 170 by using a conventional tool with the internal hex surface 176.

The abutment 120, the cylinder 150, the abutment screw 140, and the cylinder screw 170 are of known design, being standard components of the Nobelpharma Implant System. They are not described here in detaail, except as they differ from those known components.

Figure 38:
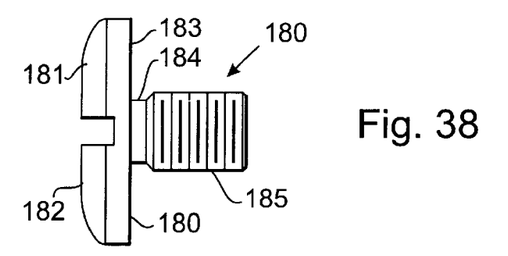
FIG. 38 is a side view of of a cover screw 180.

The cover screw 180, also called a healing screw, has a slotted head 181, an upper plane surface 182, an lower plane surface 183, an external neck 184 and an external threaded stem 185.

The cover screw 180 is inserted in the threaded aperture 111 of the subperiosteal bone anchor 102. The cover screw 180 remains in the threaded aperture 111 of the subperiosteal bone anchor 102 until the bone bonding is complete and the abutment 120, the cylinder 150, and the orthodontic device are attached. The composition of the subperiosteal bone anchor 102, the abutment 120, the abutment screw 140, the cylinder 150 and the cover screw 180 is commercially pure titanium.

Figure 23:
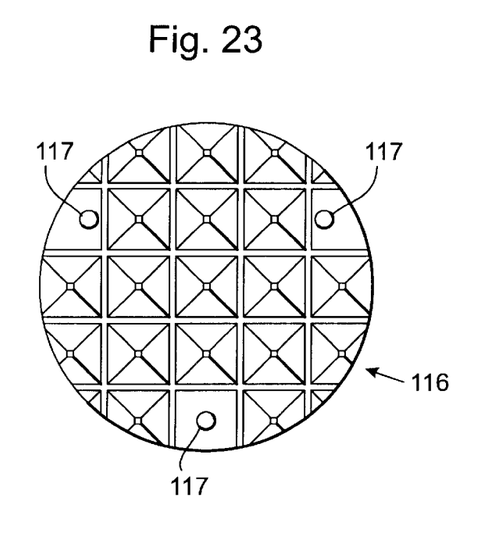
FIG. 23 is a bottom view of an alternative embodiment of the present invention, a subperiosteal bone anchor 116.
Figure 24:
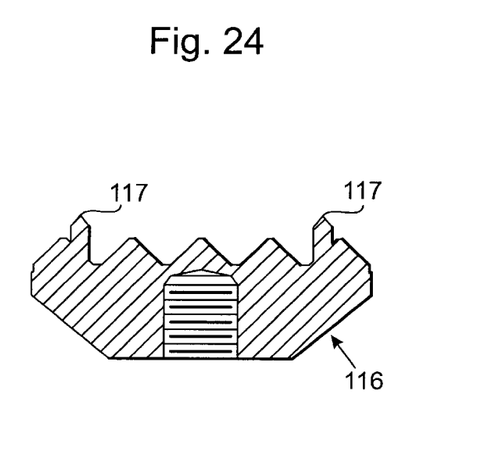
FIG. 24 is a cross sectional view of of the subperiosteal bone anchor 116 of FIG. 23.

FIGS. 23 & 24 discloses an alternative embodiment of of the subperiosteal bone anchor 102 shown in FIGS. 16–20. The subperiosteal bone anchor 116 has three talons 117 extending below the bone interface surface 103. These talons 117 are tapped into the bone when the subperiosteal bone anchor 116 is placed in the subperiosteal tunnel. The talons 117 pierce the surface of the bone and holds the subperiosteal bone anchor 116 in position as osseointegration takes place.

Figure 25:
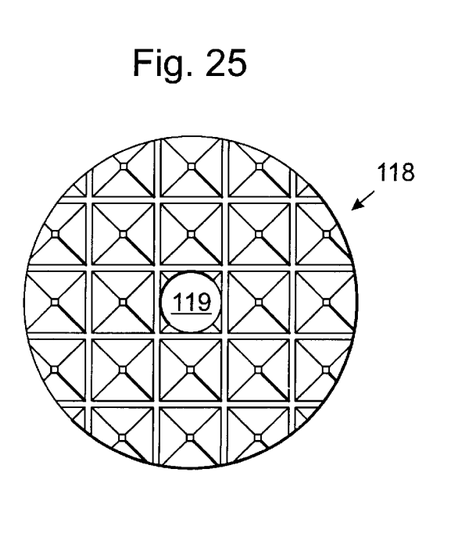
FIG. 25 is a bottom view of an alternative embodiment of the present invention, a subperiosteal bone anchor 118.
Figure 26:
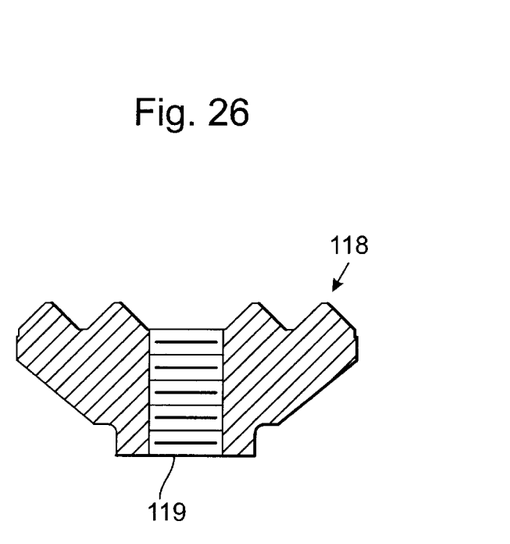
FIG. 26 is a cross sectional view of of the subperiosteal bone anchor 118 of FIG. 25.
Figure 39:
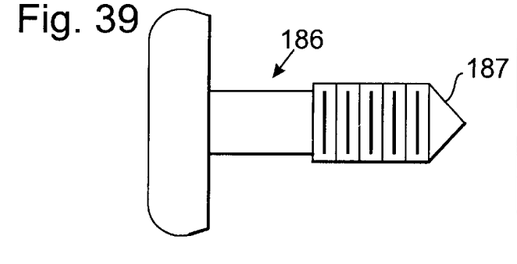
FIG. 39 is a side view of of a cover screw 186, an alternative embodiment of of the cover screw 180 of FIG. 38.
Figure 40:
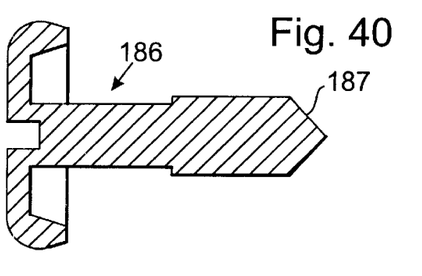
FIG. 40 is a cross sectional view of of the cover screw 186 of FIG. 39.

FIGS. 25 & 26 discloses an alternative embodiment of of the subperiosteal bone anchor 102 shown in FIGS. 16–20. The subperiosteal bone anchor 118 has a threaded through hole 119, and, as shown in FIGS. 39 & 40, a cover screw 186 with a pointed end 187. When the cover screw 186 is placed in the subperiosteal tunnel, the pointed end 187 is screwed into the threaded through hole 119, through the subperiosteal bone anchor 118, and into the bone. The threaded through hole 119 pierces the surface of the bone and holds the subperiosteal bone anchor 116 in position as osseointegration takes place.

Figure 30:
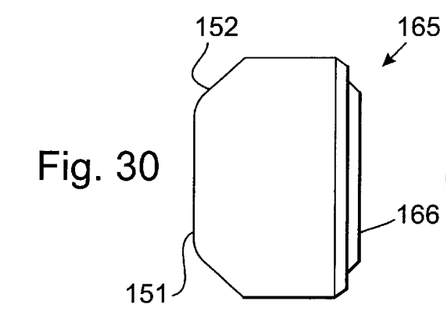
FIG. 30 is a side view of of cylinder 165, an alternative embodiment of of cylinder 150 of FIG. 27.
Figure 31:
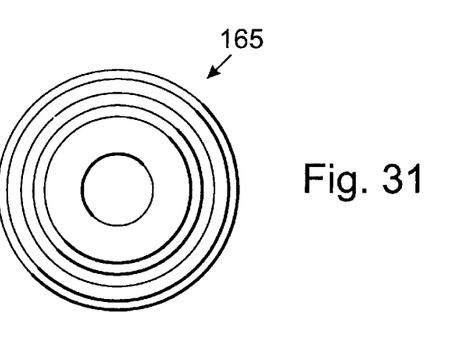
FIG. 31 is a bottom view of of the cylinder 165 of FIG. 30.
Figure 32:
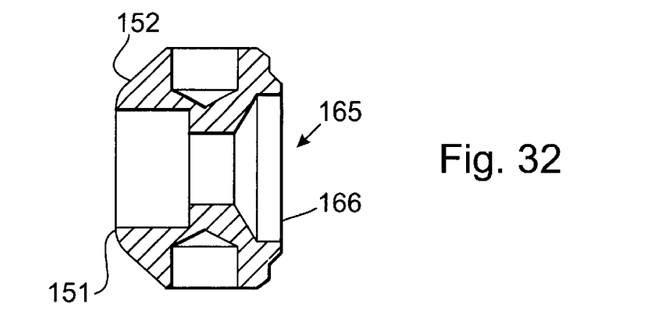
FIG. 32 is a cross sectional view of of the cylinder 165 of FIG. 30.

An alternative embodiment of permits the orthodontist to rotate the orthodontic device. As shown in FIGS. 21 & 22 & 30–32, the subperiosteal bone anchor 114 has no external hex surface. Thus the abutment 120 may rotate freely on the subperiosteal bone anchor 114 until the abutment screw 140 is tightened. As shown in FIGS. 30–32, the cylinder 165 has a internal lower tapered surface 166, in place of the external hex surface 157 as shown in FIG. 27. Thus the cylinder 165 may rotate freely on the abutment 120 until the cover screw 180 is tightened.

The abutment 120 may be of varying lengths to permit the orthodontic device to be at different distances from the bone to which the subperiosteal bone anchor 102 is bonded. In that case the internal upper cylindrical surface 130 of the abutment 120 will be made longer or shorter. The mating external cylindrical surface 142 of the abutment screw 140 will also be made longer or shorter to match.

B. Method of Treatment

The orthodontic anchor system (20) is installed in the patient's mouth in two steps. These steps are generalized for an understanding of the invention. The example will be as if the location will be between the maxillary permanent first molars.

Under local anesthesia, an anterior palatal incision will be made and a subperiosteal tunnel created so that the tunnel will place the subperiosteal bone anchor at the proposed location. Conservative dissection will be used in order that the palatal reflection is minimal and restricted to only the subperiosteal bone anchor site in order to prevent subperiosteal bone anchor migration. One or several subperiosteal bone anchors will be placed depending upon the treatment needs. Previous experience indicates that careful surgical technique will result in secure positioning of these subperiosteal bone anchors, without the need for retentive wires, etc., to maintain bone contact on the flat surfaces. However, on curved surfaces a small screw or suture may be needed to retain the subperiosteal bone anchor in the preferred position during osseointegration.

The subperiosteal bone anchor is usually provided sterile by the manufacturer. It will be placed into the subperiosteal tunnel taking great care to place it directly against the palatal bone. The incision will be closed using 4–0 polyglactin sutures. The patients will be given a prescription for antibiotics (typically penicillin or doxycycline) and analgesics. This short surgical procedure should cause minimal discomfort to the patient. The patient will be called at home by the surgeon for follow-up, and seen for suture removal one week after the surgery. The patient will be followed periodically for observation during the healing period.

Twelve weeks will be allowed for healing and osseointegration to occur. The subperiosteal bone anchor requires the same osseointegration time at that required for osseointegration of calcium hydroxylapatite coated endosseous implants. To expose the subperiosteal bone anchor, patients will be given a local anesthesia and a small incision will be made directly over the subperiosteal bone anchor exposing only the healing screw (26) covering the central circular portion (36) and that was placed into the internal thread (32) of each device. The abutment (22) is screwed into the subperiosteal bone anchor. The overlying soft tissue may be thinned to a thickness of 3 mm to allow for cleaning of the abutment shoulder. An impression will be taken to transfer the bands abutment device and palatal contours to a working cast. This working cast will be used in a dental laboratory to fabricate the palatal wire or cast palatal bar which will be soldered to the bands.

The palatal wire (28) must be rigid and of a very large diameter. Otherwise, bending of this wire will occur and some forward movement of the teeth to which it is attached will result. The palatal wire in the illustrated example was fabricated of 0.051 inch stainless steel orthodontic wire in experiments completed by the inventors. Once the fabrication is complete the wire-bands or bar-bands assembly will be attached to the subperiosteal bone anchor and cemented to the teeth to be stabilized.

In the example given, the remaining anterior teeth were retracted utilizing conventional orthodontic appliances. Since the anchored teeth did not move, the use of auxiliary devices such as head gears, intraoral elastics, or other augmenting devices was not necessary. The location of the teeth with respects to the subperiosteal bone anchors may be measured and recorded by radiographs or physical measurement.

At the conclusion of the orthodontic treatment when the device is no longer needed, the retrieval will be a very brief and simple procedure, just like the insertion. Using local anesthesia, an incision will be made exposing the entire subperiosteal bone anchor. Using forceps designed for this procedure, the subperiosteal bone anchor will be removed.

C. Report of Treatment

In a simultaneous study, two subperiosteal bone anchors were attached to the ramus of a dog. Both devices were subjected to sheer strength studies requiring 160 to 162 pounds respectively of sheer force to dislodge the calcium hydroxylapatite coated subperiosteal bone anchors. Based on these mechanical studies of subperiosteal bone anchors, the subperiosteal bone anchors will withstand continuously applied orthodontic or orthopedic forces which are generally in the range of 6 ounces to 20 pounds.

To further verify this concept, clinical trials using calcium hydroxylapatite coated dental subperiosteal bone anchors as orthodontic anchor systems (20) the inventors demonstrated that a calcium hydroxylapatite coated subperiosteal bone anchor placed on the bone of the maxilla can be used as an anchor for orthodontic treatment. Teeth attached to these subperiosteal bone anchors did not move, whereas those teeth not stabilized by the subperiosteal bone anchors moved noticeably when subjected to the reciprocal force.

The surface of the subperiosteal bone anchor which will rest against the bone may be textured, as shown, to increase the surface area and resist sheer forces. This is not necessary if a smooth surfaced device osseointegrates with adequate strengths for the designed force loads. If the subperiosteal bone anchor is a biologically inactive substance it must be coated with a osseoactive material such as calcium hydroxylapatite to promote osseointegration. If the subperiosteal bone anchor itself is osseoactive, such as a plastic or collagen, then additional coating with a osseoactive material may be unnecessary.

D. Orthopedic Applications

The subperiosteal bone anchor may be used as an anchor for an orthopedic device in order to guide the movement of bones to bring them closer together or further apart for the correction of bone deformities or injuries using the concepts of distractive osteogenesis. This technique was perfected by a Russian orthopedist, Dr. Gavriel A. Ilizarov, who teaches us that if a cortical surface of a long bone is incised the medullary or cancellous portion of the bone may be stretched or expanded. Significant bone elongations of 6" to 8" have been realized. The expansion devices are commonly attached to the bone fragments using transosseous pins threaded into the medullary spaces. There is a need in orthopedic treatment for a surface adherent device which does not penetrate into the medullary spaces. Distraction osteogenesis has been successfully adapted to human mandibles. Transosseous devices in a juvenile would be hazardous because the body of the mandible is filled with developing tooth buds. To use a transosseous device or a pin in the adult may be difficult unless there are edentulous areas into which the pins can be inserted.

Figure 12:
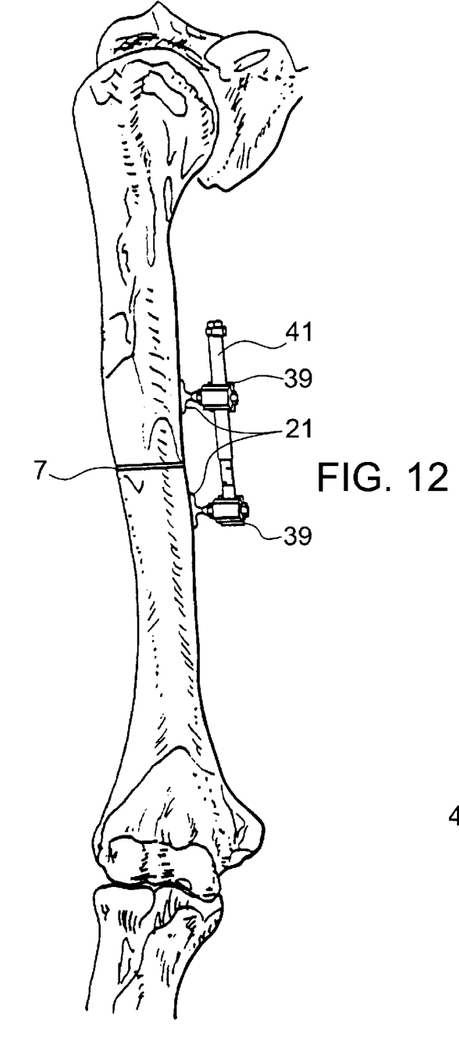
FIG. 12 is an illustration of a long bone with two subperiosteal bone anchors of this invention attached to skin penetrating abutments to which an orthopedic distraction device is attached.

FIG. 12 is an illustration of a long bone with two subperiosteal bone anchors (21) osseointegrated with the surface of the bone. The cortical surface of the bone has been incised (7) leaving the medullary portion intact. Abutments (39) are attached to the subperiosteal bone anchors (21) and exit the skin. A conventional osteogenic distraction device (41) is shown attached to the abutment. Activation of the expansion device will cause the bone segments to move apart at the rate of 1 mm per day.

Figure 13:
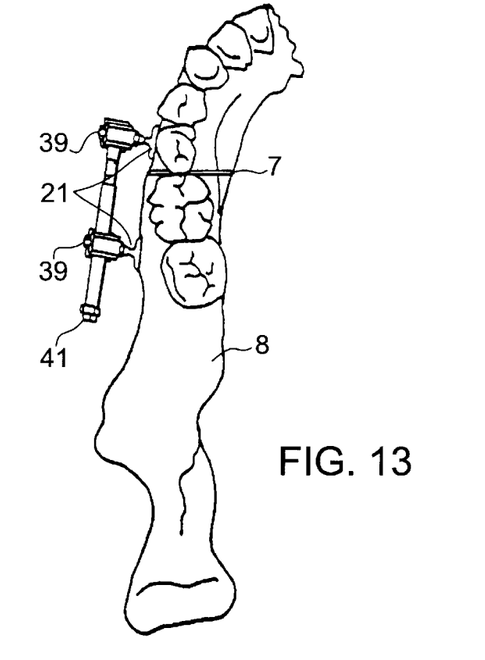
FIG. 13 shows the adaptation of the above distraction device to the human mandible.

FIG. 13 shows the adaptation of the distraction osteogenesis to the human mandible (8). Two subperiosteal bone anchor (21) have osseointegrated with the bone. The cortical surfaces have been incised (7) and skin penetrating abutments (39) are attached to a commercially available distraction device (41).

Figure 11:
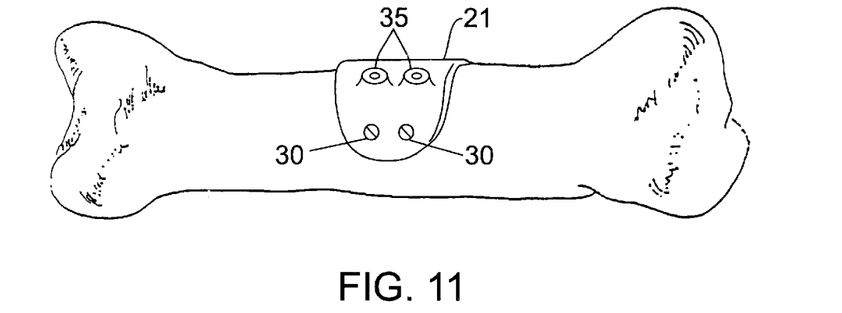
FIG. 11 shows an alternative embodiment of the invention to fit a convex bone surface.
Figure 14:
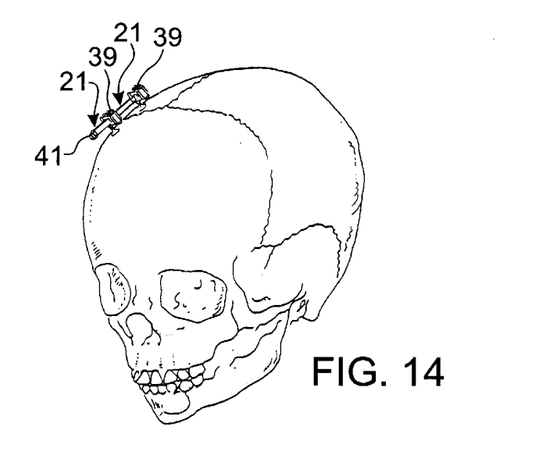
FIG. 14 shows the adaptation of the above distraction device to the human skull.

FIG. 14 illustrates the application of subperiosteal bone anchors (21) to cranial bones. Once osseointegration has occurred commercially available expansion device(s) (41) will be attached to skin penetrating abutments (39). Activation of these expansion devices will cause the bones to separate to yield a more concentric shape to the skull. In certain cases, such as a finger bone, FIG. 11, the subperiosteal bone anchor could be held in place during osseointegration by sutures or by the stabilization screw (30). The stabilization screw (30) is meant to stabilize the position of the subperiosteal bone anchor while integration is taking place. The stabilization screw (30) is not meant to anchor the subperiosteal bone anchor to the bone during the loading period. The stabilization screw (30) will be removed by the surgeon when the subperiosteal bone anchor is exposed and the abutment is screwed in place.

After osseointegration the orthopedic expansion devices are attached to two or more subperiosteal bone anchors on the bone or bones to transmit attractive or distractive forces for bone transformation. Alternatively, the subperiosteal bone anchor (21) such as that of a finger bone, as in FIG. 11, could be used as a prosthetic anchor for an artificial finger tip.

E. Other Applications

Figure 9:
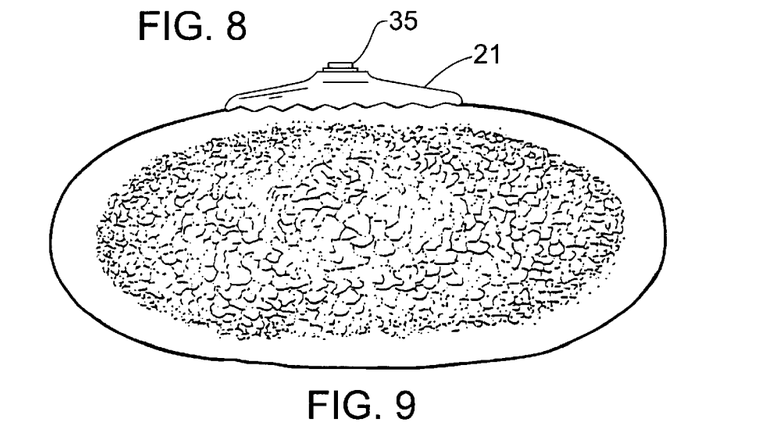
FIG. 9 is a cross-sectional view of a skeletal long bone showing the invention on the surface.
Figure 10:
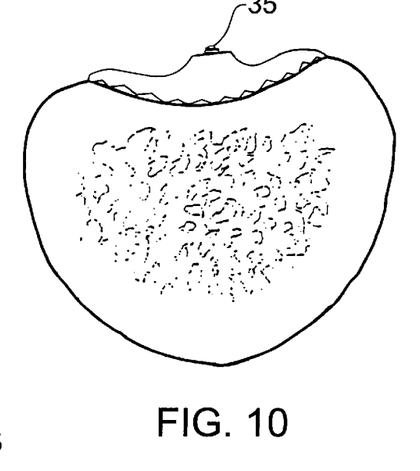
FIG. 10 shows an alternative embodiment of the invention to fit a concave bone surface.

The invention may be used to attach a medical device. FIG. 9 shows subperiosteal bone anchor (21) on a rib bone. A suitable attachment means (35) is shown generally. A pacemaker may be attached to it, which provides a more stable mounting than is conventionally used today. This invention may also have similar application in veterinary medicine.

It will thus be seen that the objects set forth above, among those made apparent from the preceding description, are efficiently attained and, since certain changes may be made in carrying out the above method and in the article set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A subperiosteal bone anchor having:

a) a first surface, being the entire area on one side of the subperiosteal anchor, said first surface being substantially flat to match the cortical surface of the palatal bone, said first surface comprising a bone interface surface;

b) said first surface comprising a means for attachment to the original exterior cortical surface, said attachment means comprising a calcium hydroxylapatite coating whereby said first surface osseointegrates with the original exterior cortical surface of said bone;

c) said first surface having a major axis from one to two times its minor axis;

d) said subperiosteal bone anchor having a second surface opposite said first surface and said second surface having means thereon to attach an orthodontic or orthopedic device;

e) said subperiosteal bone anchor being substantially rigid and thin at its periphery;

f) said subperiosteal bone anchor preformed to be located entirely on the original exterior cortical surface of the palatal bone;

WHEREBY said subperiosteal bone anchor permits said orthodontic or orthopedic device to apply or resist a continuous force to an adjacent tooth or bone, is applied in a simple single surgical procedure, does not disturb the cortical surface or invade the medullary contents of the bone, is designed for temporary application and is easily retrievable.

2. The combination of claim 1 wherein said first surface is uninterrupted and thus free of any apertures or perforations.

3. The combination of claim 1 wherein said first surface is circular.

4. The combination of claim 1 wherein said second surface has a threaded aperture with an axis normal to said surface.

5. The combination of claim 4 wherein said means to attach an orthodontic device includes a protruding threaded screw cooperating with said threaded aperture.

6. The combination of claim 1 wherein said anchor is of a size and shape to fit against the palatal bone of a human.

7. A method of orthodontic or orthopedic treatment using a retrievable subperiosteal bone anchor with a single operation to place the bone anchor, comprising the steps of:

a) making an incision to expose the cortical surface of the bone to which the subperiosteal bone anchor is to be placed;

b) selecting a subperiosteal bone anchor having a first surface, said first surface being the entire area on one side of the subperiosteal anchor, said first surface being substantially flat to match the original exterior cortical surface of the bone to which it is to be attached, said first surface having a major axis from one to two times its minor axis, said subperiosteal bone anchor having a second surface opposite said first surface and said second surface having means thereon to attach a orthodontic or an orthopedic device, said subperiosteal bone anchor being substantially rigid and thin at the periphery;

c) said first surface having a calcium hydroxylapatite coating whereby said first surface osseointegrates with the cortical surface of the bone;

d) locating said subperiosteal bone anchor entirely on the original exterior cortical surface of the bone;

e) closing the incision to allow the site to heal and for osseointegration to occur whereby said first surface osseointegrates with the original exterior cortical surface of the bone;

f) after healing and osseointegration, attaching an orthodontic or orthopedic device to said means on said second surface;

g) after completion of the treatment, removing the subperiosteal bone anchor, and permitting the site to heal;

WHEREBY a subperiosteal bone anchor is placed onto the cortical surface of a selected bone with a single operation and the selected orthodontic or orthopedic device is thereafter attached.

8. The method of claim 7 wherein said first surface is uninterrupted and thus free of any apertures or perforations.

9. The method of claim 7 wherein said anchor is of a size and shape to fit against the palatal bone of a human.

10. A subperiosteal bone anchor having:

a) a first surface, being the entire area on one side of the subperiosteal anchor, said first surface being preformed to match the cortical surface of a selected bone, said first surface comprising a bone interface surface;

b) said first surface comprising a means for attachment to the original exterior cortical surface, said attachment means comprising an osseointegratable coating whereby said first surface osseointegrates with the original exterior cortical surface of said bone;

c) said subperiosteal bone anchor having a second surface opposite said first surface and said second surface having means thereon to attach an orthodontic or an orthopedic device;

d) said subperiosteal bone anchor being substantially rigid and thin at its periphery;

f) said subperiosteal bone anchor preformed to be located entirely on the original exterior cortical surface of the bone;

WHEREBY said subperiosteal bone anchor permits said orthodontic or orthopedic device to apply or resist a continuous force to an adjacent tooth or bone, is applied in a simple single surgical procedure, does not disturb the cortical surface or invade the medullary contents of the bone, is designed for temporary application and is easily retrievable.

11. The combination of claim 10 wherein said first surface is substantially flat.

12. The combination of claim 10 wherein said first surface has a major axis from one to two times its minor axis.

13. The combination of claim 10 wherein said first surface is circular.

14. The combination of claim 10 wherein the first surface is uninterrupted and thus free of any apertures or perforations.

15. The combination of claim 10 wherein said coating is calcium hydroxylapatite.

16. The combination of claim 10 wherein said second surface has a threaded aperture normal to said surface.

17. The combination of claim 16 wherein said means to attach an orthodontic or orthopedic device includes a protruding threaded screw cooperating with said threaded aperture.

18. The combination of claim 10 including a internal threaded aperture with an axis normal to the first surface and passing from said first surface to said second surface, and a cover screw having external threads cooperating with said internal threads, said cover screw having a length sufficient to pass through the anchor, said cover screw having a pointed end, whereby said cover screw pierces the bone and holds said anchor in place during osseointegration.

* * * * *

UNITED STATES PATENT AND TRADEMARK OFFICE
CERTIFICATE OF CORRECTION

PATENT NO. : 5,769,630

DATED : June 23, 1998

INVENTOR(S) : Hoffman et al.

It is certified that error appears in the above-identified patent and that said Letters Patent is hereby corrected as shown below:

On the title page, under item [19], "Hoffman" should read --Hoffman et al--
On the title page, item [75] Inventors, insert the following, --; Michael S. Block, Metarie, LA.--.

Signed and Sealed this

Twenty-fourth Day of November,1998

Attest:

BRUCE LEHMAN

*Attesting Officer*     *Commissioner of Patents and Trademarks*